United States Patent
Kuhns et al.

(10) Patent No.: US 9,173,546 B2
(45) Date of Patent: Nov. 3, 2015

(54) DIAGNOSTIC DEVICE FOR TUBULAR ANATOMICAL STRUCTURES

(75) Inventors: Jesse J. Kuhns, Cincinnati, OH (US); Michele D'Arcangelo, Via Benedetto Croce (IT); Federico Bilotti, Aprilia (IT); Antonio Longo, Palermo (IT)

(73) Assignee: Antonio Longo, Palermo (IT)

( * ) Notice: Subject to any disclaimer, the term of this patent is extended or adjusted under 35 U.S.C. 154(b) by 391 days.

(21) Appl. No.: 10/579,014

(22) PCT Filed: Nov. 16, 2004

(86) PCT No.: PCT/IT2004/000629
§ 371 (c)(1),
(2), (4) Date: May 8, 2006

(87) PCT Pub. No.: WO2005/048828
PCT Pub. Date: Jun. 2, 2005

(65) Prior Publication Data
US 2007/0149845 A1    Jun. 28, 2007

(30) Foreign Application Priority Data
Nov. 21, 2003   (IT) .............................. MI2003A2278

(51) Int. Cl.
| A61M 29/00 | (2006.01) |
| A61B 1/00 | (2006.01) |
| A61B 1/31 | (2006.01) |
| A61B 1/32 | (2006.01) |

(52) U.S. Cl.
CPC ......... *A61B 1/00085* (2013.01); *A61B 1/00087* (2013.01); *A61B 1/31* (2013.01); *A61B 1/32* (2013.01)

(58) Field of Classification Search
CPC .. A61B 1/32; A61B 19/24; A61B 2017/3484; A61M 29/00
USPC .......... 606/197, 198, 191; 600/105, 184, 203, 600/210, 219; 604/104, 106
See application file for complete search history.

(56) References Cited

U.S. PATENT DOCUMENTS

| 1,950,788 | A | * | 3/1934 | Ewerhardt et al. ............ 607/138 |
| 2,621,651 | A | * | 12/1952 | Wallace ........................ 600/104 |
| 3,044,461 | A | | 7/1962 | Murdock |
| 3,495,566 | A | | 2/1970 | Pall |
| 3,667,474 | A | * | 6/1972 | Lapkin et al. ................. 606/198 |
| 3,882,852 | A | * | 5/1975 | Sinnreich ...................... 600/104 |

(Continued)

FOREIGN PATENT DOCUMENTS

DE    19828099 A1 * 12/1999
WO   WO 2005/048828 A1   6/2005

*Primary Examiner* — Katherine Rodjom
(74) *Attorney, Agent, or Firm* — Nixon & Vanderhye P.C.

(57) ABSTRACT

A diagnostic device (10) for pathologies of tubular anatomical structures comprises a tubular elongated structure (12, 28) developing between a proximal end and a distal end and is adapted to be inserted in the tubular anatomical structure, means (22) for locally dilating the walls of the tubular anatomical structure being associated with the distal end of said elongated structure, said means for locally dilating being movable between a closed position for introducing the device and at least one open position for viewing and evaluating the pathology, and control means being associated with the proximal end of the elongated structure, said control means being operatively connected to said means for locally dilating, in order to move them between the closed position and the open position, and vice versa.

13 Claims, 15 Drawing Sheets

(56) References Cited

U.S. PATENT DOCUMENTS

| | | | |
|---|---|---|---|
| 4,865,030 A * | 9/1989 | Polyak | 606/108 |
| 5,178,133 A * | 1/1993 | Pena | 600/203 |
| 5,353,784 A * | 10/1994 | Nady-Mohamed | 600/205 |
| 5,377,667 A * | 1/1995 | Patton et al. | 600/184 |
| 5,556,376 A * | 9/1996 | Yoon | 604/15 |
| 5,972,004 A * | 10/1999 | Williamson et al. | 606/142 |
| 6,638,247 B1 * | 10/2003 | Selmon et al. | 604/104 |
| 6,855,107 B2 | 2/2005 | Avni et al. | |
| 2005/0159645 A1 * | 7/2005 | Bertolero et al. | 600/116 |
| 2006/0079925 A1 * | 4/2006 | Kerr | 606/198 |

* cited by examiner

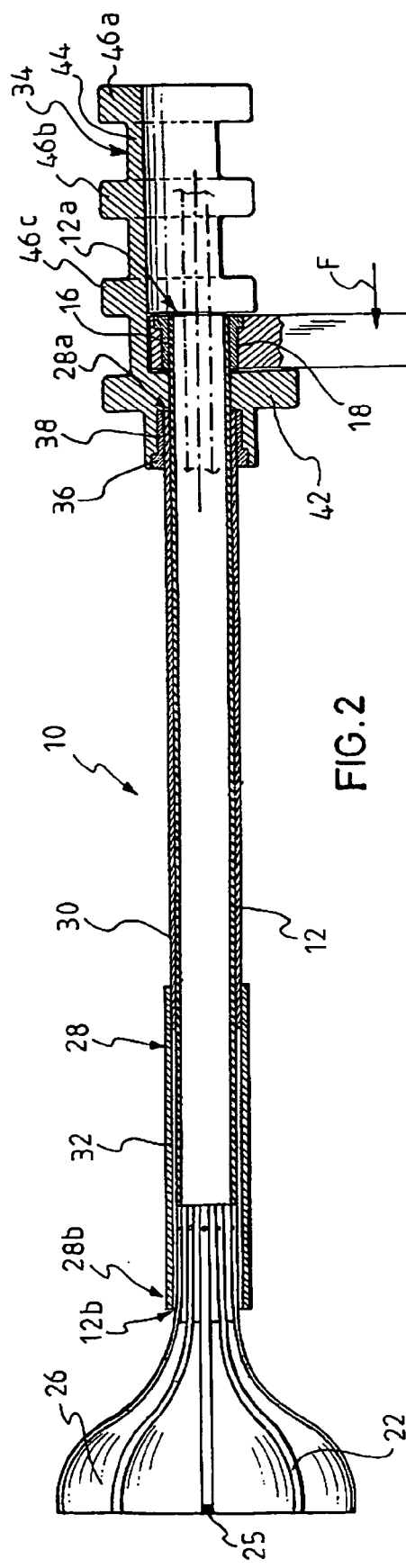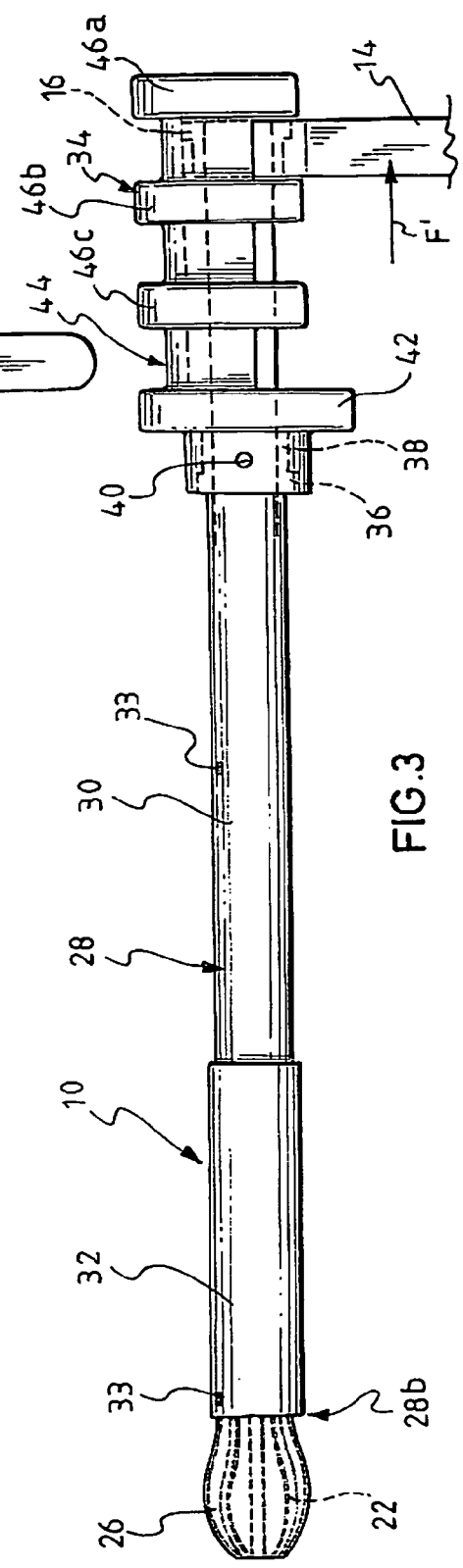

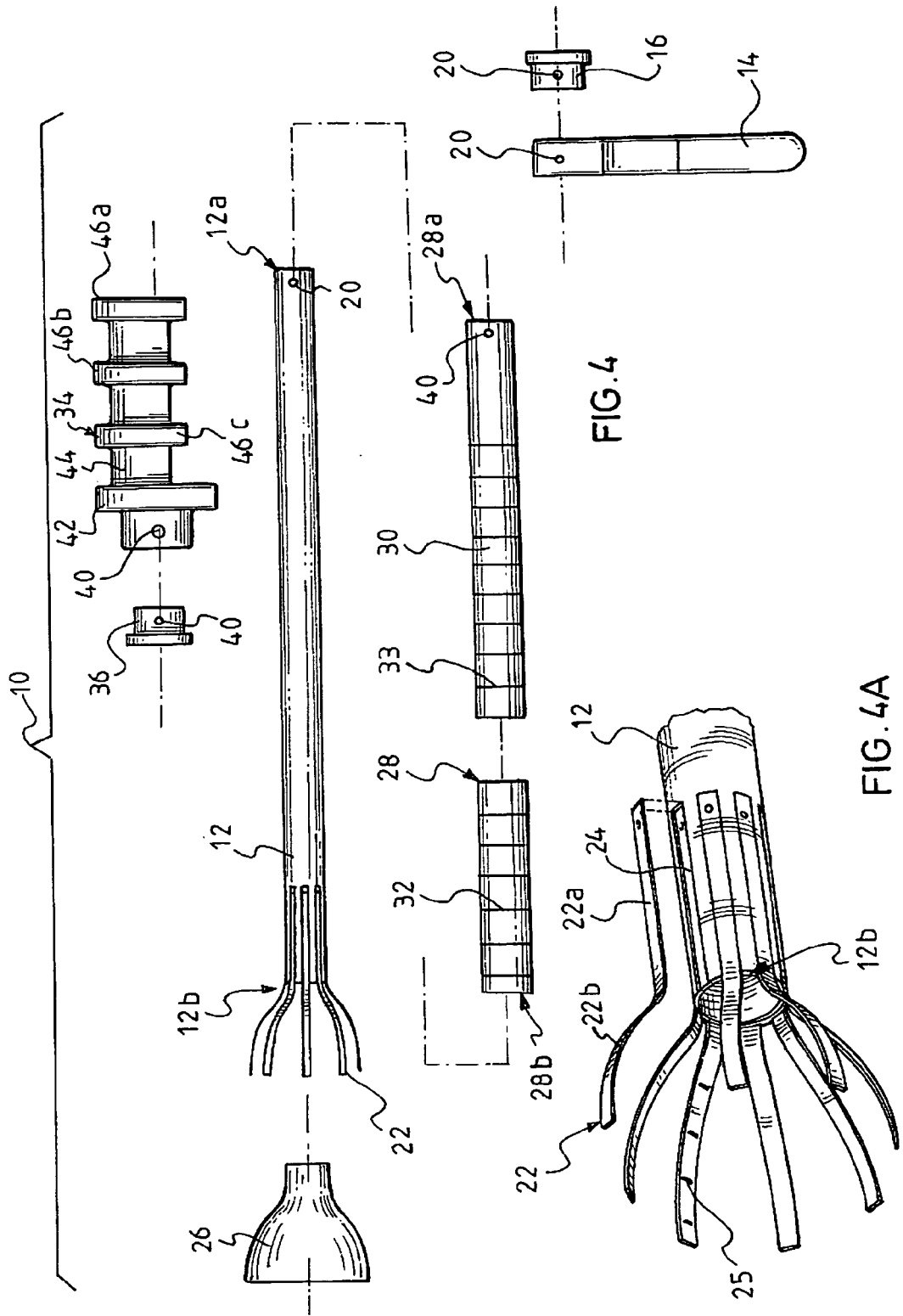

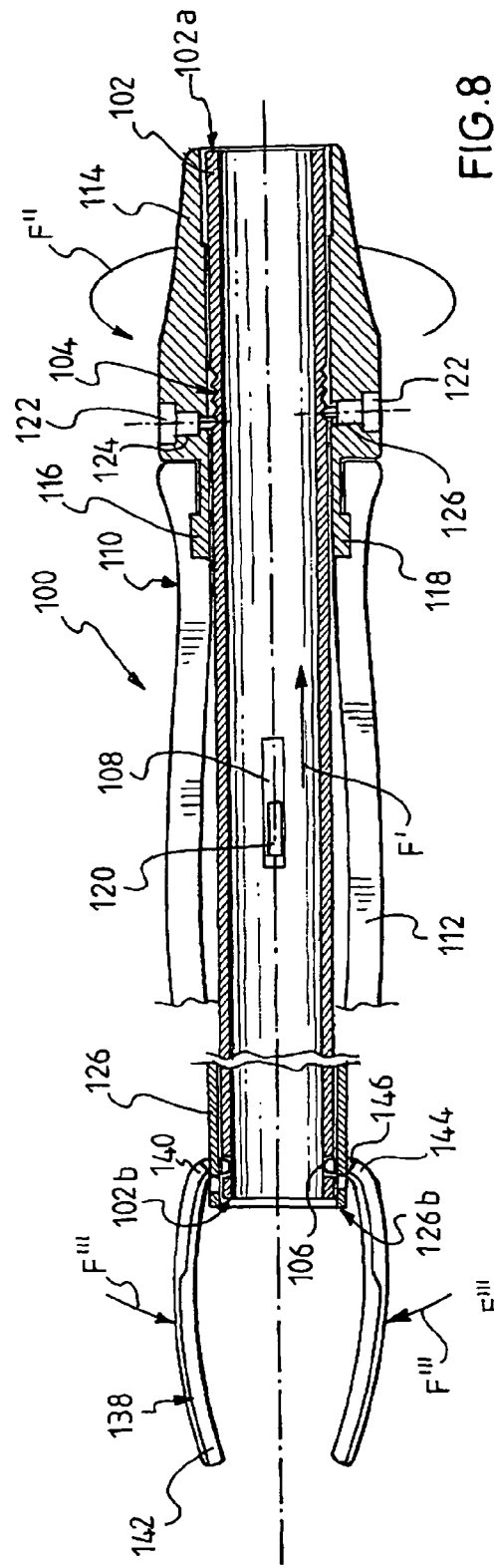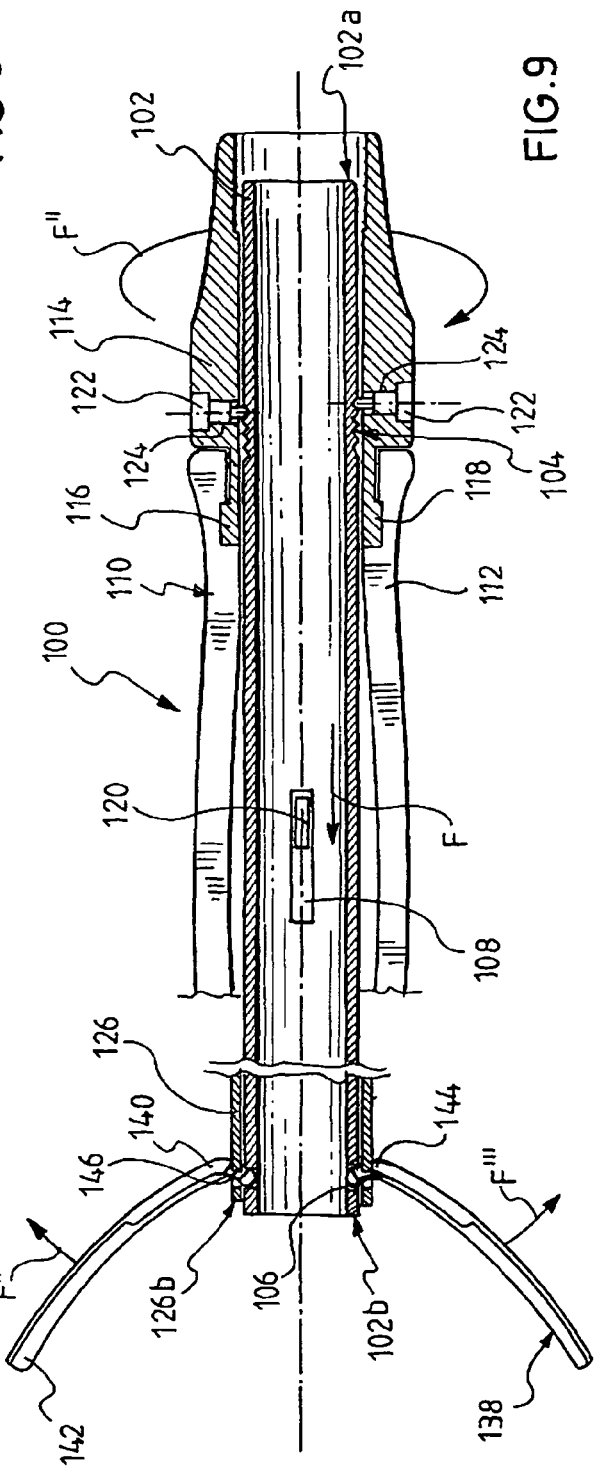

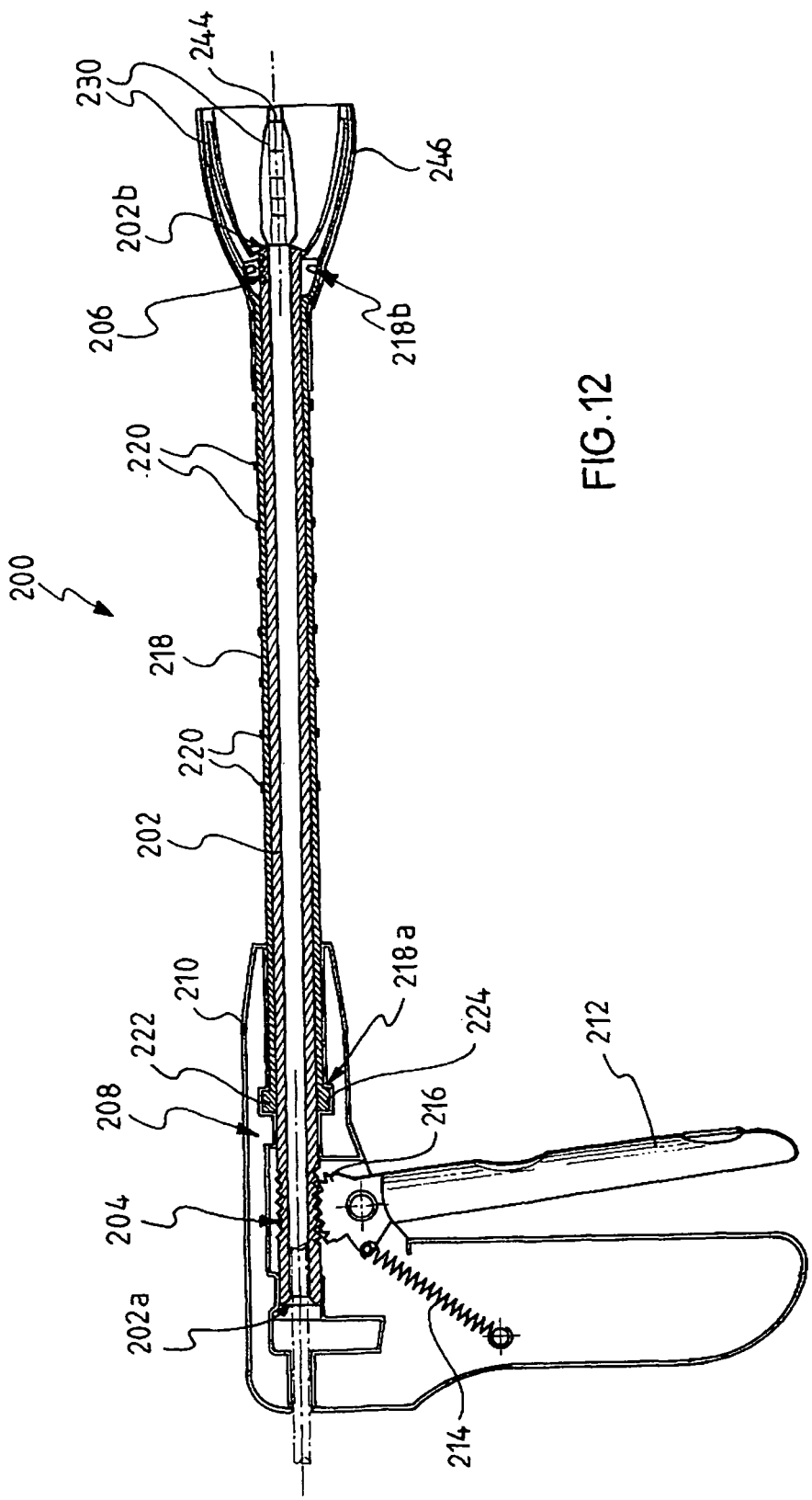

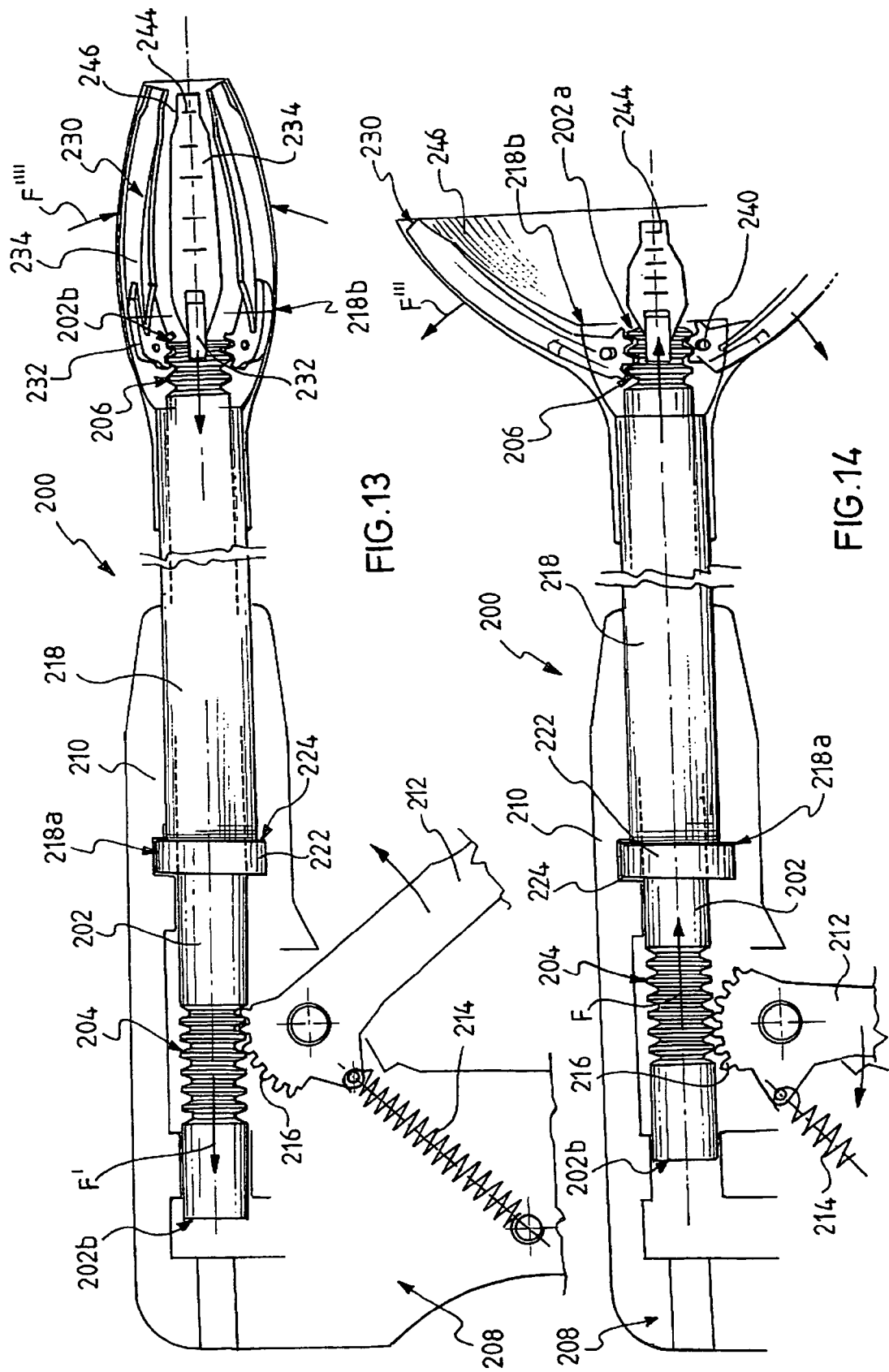

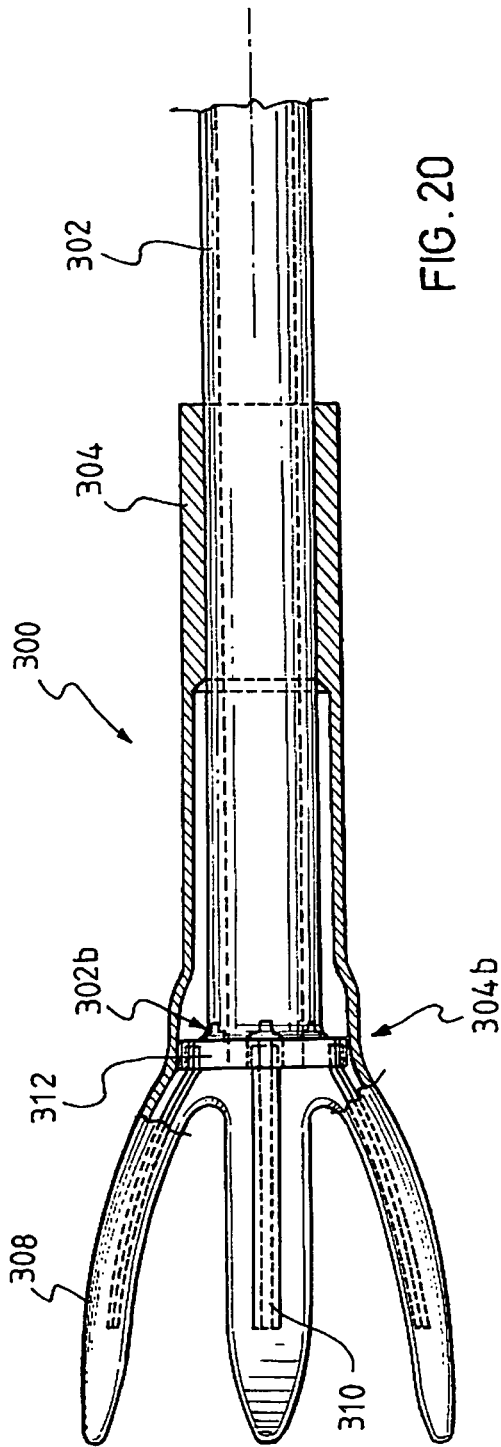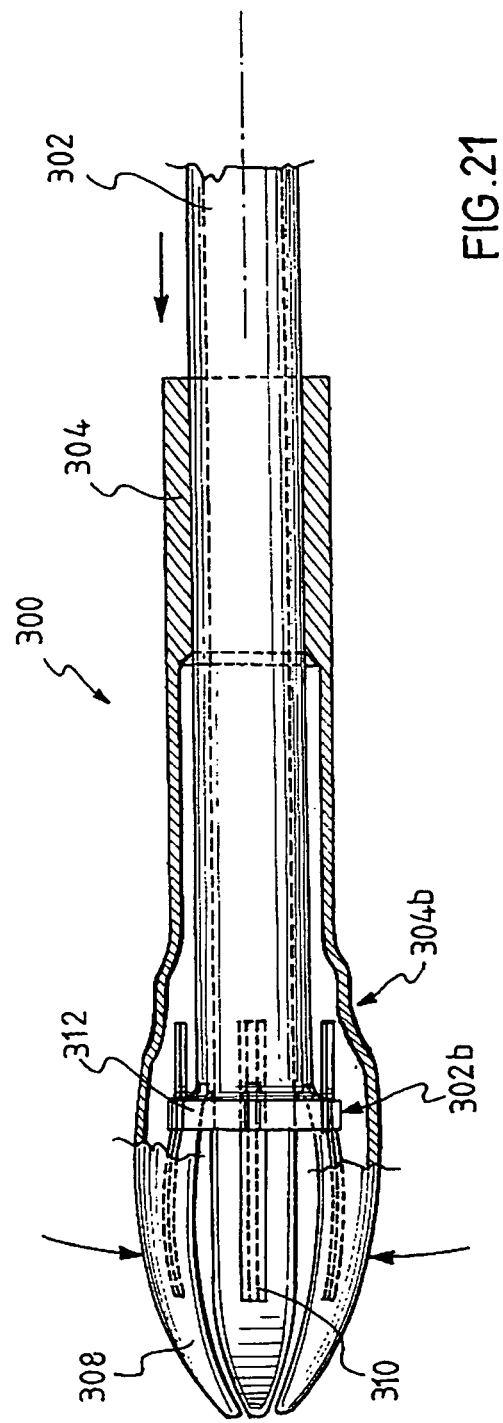

DIAGNOSTIC DEVICE FOR TUBULAR ANATOMICAL STRUCTURES

A diagnostic device for the pathologies of tubular anatomical structures, such as for example the intestinal tracts, is the subject of the present invention. In particular, the present invention refers to a diagnostic device for pathologies of the colon or the rectum such as for example intussusception, stenosis, prolapse, rectocele.

The need for the availability of a diagnostic device for the aforementioned pathologies, which is realisable with limited expense, usable even in non hospital or clinical structures and which gives rise to the least possible discomfort in patients, avoiding for example the administration of sedatives, is particularly felt within the sector. In addition, the need for the availability of a diagnostic device which allows the verification of the presence and the nature of a mucosal prolapse is particularly felt.

Diagnostic devices, such as flexible colonoscopes and sigmoidoscopes which have significant drawbacks are known. Generally, colonoscopes work by the insufflation of air in order to dilate the walls of the intestinal tract subjected to analyses. The insufflation of air gives rise to significant discomfort in the patients and frequently it is necessary to resort to the administration of sedatives. Furthermore, the insufflation of air causes dilation of the rectum with the consequence that any possible mucosal prolapse disappears and may not be viewed.

Anoscopes which allow the direct vision of the area involved and which can also be of large dimensions, for example with diameters greater than 2 cm, are also known, causing pain during insertion and requiring the relaxation of the sphincter.

Due to the complexity and the expense of the equipment required, in addition to the high discomfort which they cause in patients, frequently the only structures which are so equipped are hospitals or clinics, requiring therefore that the majority of the diagnostic procedures be carried out in such environments.

The problem at the heart of the present invention is that of proposing a diagnostic device for the pathologies of the intestinal tracts, in particular of the rectum and colon, which has structural and operational characteristics such as to satisfy the aforementioned needs and to overcome the aforementioned drawbacks cited in reference to the known art.

Such a problem is solved by a diagnostic device in agreement with claim 1. The dependent claims refer to further embodiments of the device according to the present invention.

Further characteristics and advantages of the diagnostic device according to the invention will arise from the following reported description of its preferred example embodiments, given for non-limiting indication, with reference to the attached figures, wherein:

FIG. 2 shows a partially sectional side view of the diagnostic device from FIG. 1;

FIG. 3 shows a side view of the diagnostic device from FIG. 1 in a different operating condition;

FIG. 4 shows an exploded side view of the diagnostic device from FIG. 1;

FIG. 4A shows a partial perspective view of a detail of the diagnostic device from FIG. 1, where several details have been omitted in order to enhance other ones;

FIG. 8 shows a partially sectional side view of the diagnostic device from FIG. 5;

FIG. 9 shows a partially sectional side view of the diagnostic device from FIG. 5, in a different operating condition relative to the view from FIG. 8;

FIG. 12 shows a sectional side view of the diagnostic device from FIG. 11;

FIG. 13 shows an enlarged sectional side view of a detail of the diagnostic device from FIG. 11;

FIG. 14 shows the detail from FIG. 13 in a different operating condition;

FIG. 20 is a longitudinal sectional side view of the detail from FIG. 18 in a first operating condition;

FIG. 21 is a longitudinal sectional side view of the detail from FIG. 18 in a second operating condition.

Figure 1:
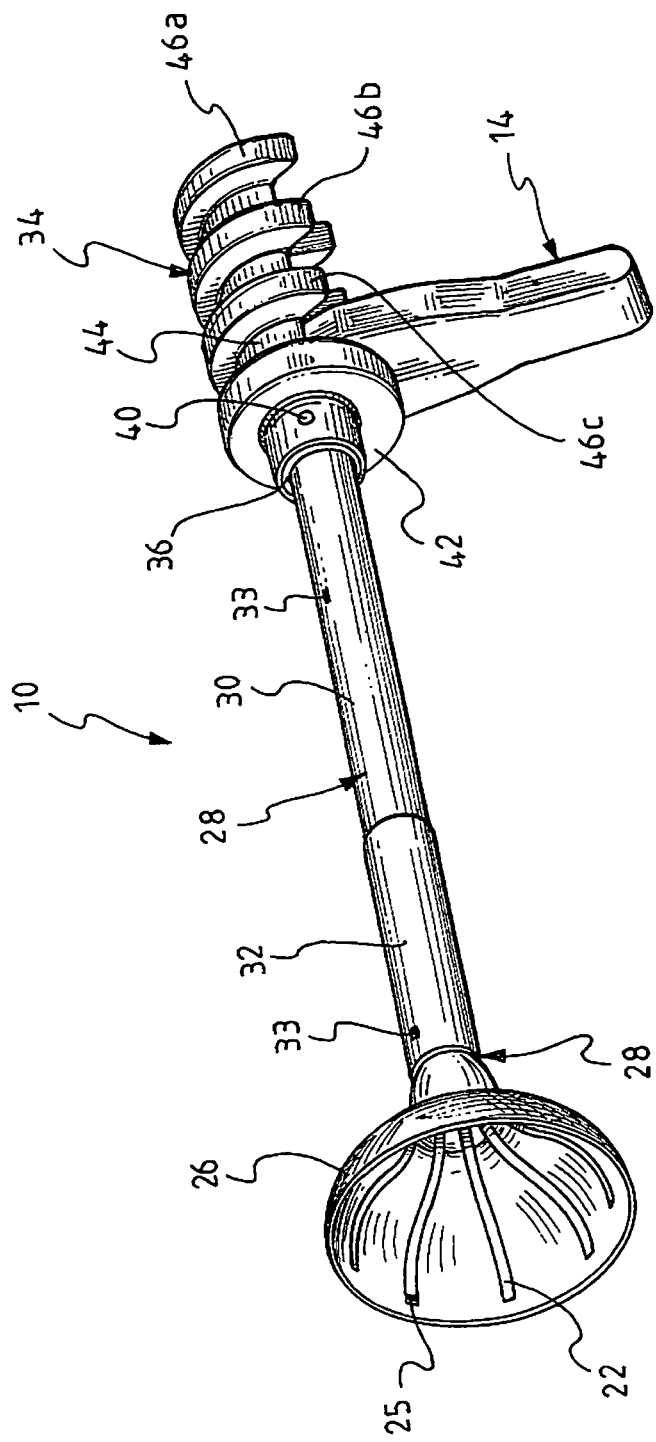
FIG. 1 shows a perspective view of an embodiment of the diagnostic device according to the present invention.
Figure 5:
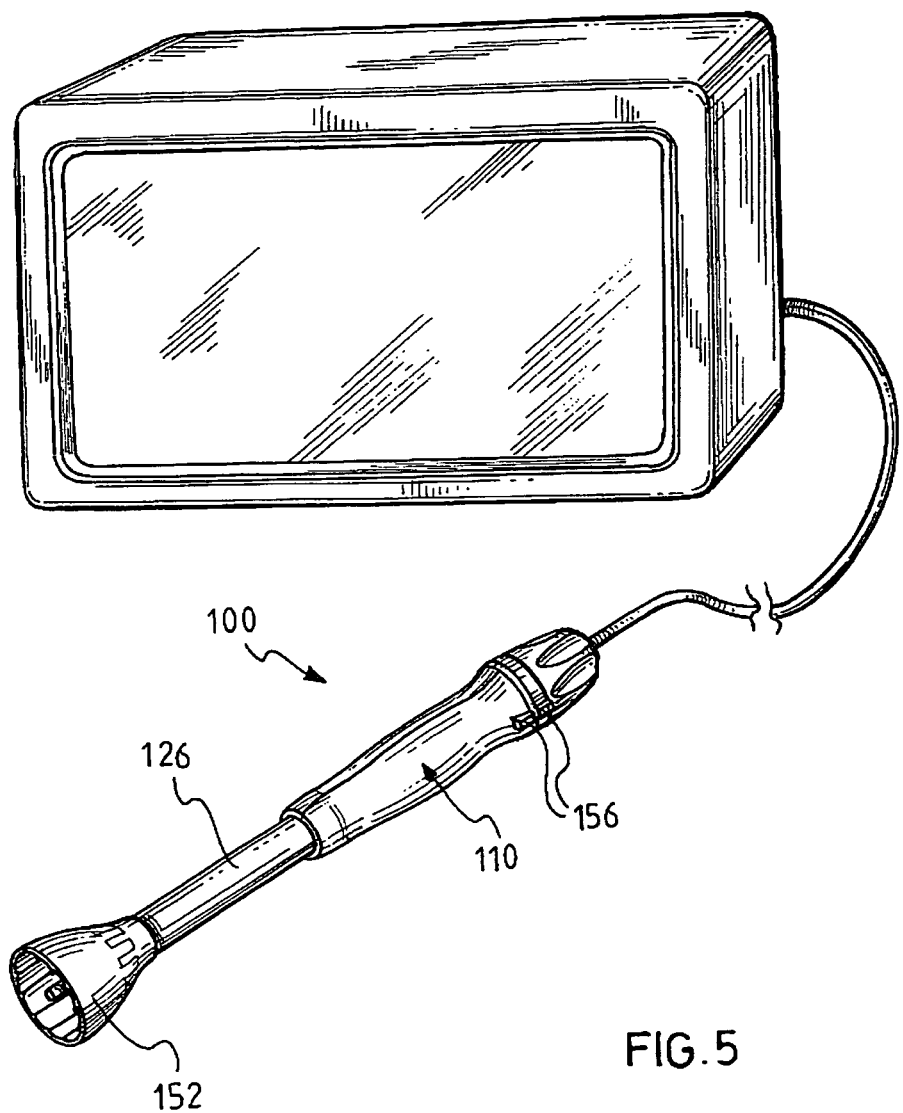
FIG. 5 shows a perspective view of an embodiment of the diagnostic device according to the present invention.

The present invention refers generically to a diagnostic device for pathologies of tubular anatomical structures, such as the intestinal tracts for example of the rectum and colon. In general terms the device advantageously comprises an elongated structure which develops between a proximal end and a distal end and which is suitable for being inserted within the anatomic structure to be examined. Moreover means for locally dilating the walls of the tubular structure associated with the distal end of the elongated structure are provided. The means for dilating are movable between a closed position for the introduction of the device and at least one open position for the viewing and the evaluation of the pathology.

The means for locally dilating are operatively connected with control means associated with the proximal end of the elongated structure. These control means are operated by the operator in order to open or close the dilating means.

In addition, visualising means suitable for being associated with the elongated structure and for reaching the tract dilated by the means of dilating are provided.

In general terms, applicable to whatsoever embodiment of the device according to the present invention, by proximal is conventionally meant a part or end of the device which, whilst in use, is near to the operator holding the device and carrying out the examination, whilst by distal is conventionally meant a part or end of the device which, whilst in use, is remote with respect to the operator carrying out the examination. Additionally, by the term advancement is meant a movement, preferably translation, carried out in the direction from the proximal end towards the distal end (for example along the arrow F of FIG. 2), whilst by withdrawal is meant a movement, preferably translation, carried out in the direction from the distal end towards the proximal end (for example along the arrow F' of FIG. 3).

In the following will be described some embodiments of such a device, for example with reference to the attached figures.

With reference to the FIGS. 1-4A, by 10 has been generally indicated a trans-anal diagnostic device according to a first possible embodiment.

By 12 has been indicated an inner tube, preferably cylindrical in shape and internally hollow. The inner tube 12 may be for example in semi-rigid or flexible material, for example in plastic material.

The inner tube 12 extends between a proximal end 12a and a distal end 12b. The proximal end 12a is operatively associated with a holding body 14, for example in the shape of a handle. According to one possible embodiment, on the proximal end 12a is inserted a fixing ferrule 16 adapted to being housed within a seat 18 of the holding body 14. Possible through holes 20 may be envisaged in the proximal end of the inner tube 12, in the fixing ferrule 16 and in the holding body 14 in order to make the three elements join together by suitable, not illustrated, means of fixing.

The distal end 12b of the inner tube is operatively associated with elastic or in any case expandable arms 22, which extend preferably in a longitudinal direction with respect to the inner tube 12. According to one possible embodiment, for example illustrated in the FIGS. 1-4A, the arms 22 are arranged in such a manner that their first end is fixed to the exterior wall of the inner tube 12 whilst a second end protrudes with respect to the distal end 12b of the inner tube 12.

According to one possible embodiment, starting from the distal end 12b of the inner tube 12, the external surface of the inner tube 12 has grooves 24, preferably longitudinal. Each groove is adapted to receiving at least one part of an arm 22. In the case in which the arms 22 have a rectangular shaped cross section, the grooves 24 have cross sections of analogous shape and size in order to receive at least one part of the aforementioned arms.

The arms 22 are suitable for assuming at least two extreme configurations corresponding to a closed configuration (FIG. 3) and a completely open configuration (FIG. 2). According to one possible embodiment, in the open configuration of the arms 22 each of them has a straight length 22a and a curved length 22b. The straight length is for example adapted to be fixed to the exterior wall of the inner tube 12.

The fixing of the arms 22 to the inner tube 12 may be made by any means, for example by gluing or welding.

The curved length of the arms is preferably such that the arms themselves in the open configuration define the framework of a substantially "cup-shaped" structure (FIG. 2). In addition the curved length of the arms 22 is preferably such that the arms themselves in the closed configuration define the framework of an "olive-shaped" or conical structure with a rounded tip (FIG. 3).

According to one possible embodiment, the arms 22 have, preferably within their interior, detection elements or radiopaque markers 25. For example all the arms 22, or only some of them, may have one or more markers 25 distributed along the length of the arm itself in order to measure the nature of the pathology encountered. As an example, in FIG. 4A the markers 25 have been shown in only one of the arms even if they may be provided on every arm and they may be provided in number and shape different from what has been shown.

According to one possible embodiment, a membrane 26 preferably made from plastic or foldable material is put on the distal end 12b of the inner tube 12 and exteriorly to the arms 22. According to one possible embodiment, the membrane is made from transparent material.

By 28 has been generally indicated an outer tube preferably comprising a first part 30 and a second part 32. In the assembled configuration of the device 10, the outer tube 28 accepts the inner tube 12 inside it. Still with reference to the outer tube 28 it is possible to identify a proximal end indicated by 28a and a distal end indicated by 28b. According to one possible embodiment, the outer tube can be made of semi-rigid or flexible material, for example of plastic material.

According to one possible embodiment, the outer tube 28 may have one or more detection elements or markers 33, for example distributed along the length of the outer tube itself, in order to measure the length of penetration of the device inside the anus. According to one possible embodiment the markers 33 have the shape of circular rings arranged transversal to the tube and distributed along the length of the outer tube itself. In FIG. 4 have been shown as an example some markers 33 which could be provided in number and shape different from what has been shown.

An additional holding body 34 is operatively associated with the proximal end 28a of the outer tube 28. According to one possible embodiment, on the proximal end 28a of the outer tube 28 is inserted a fixing ferrule 36 adapted to being housed within a seat 38 of the additional holding body 34. Possibly, through holes 40 can be envisaged in the proximal end 28a of the outer tube 28, in the fixing ferrule 36 and in the additional holding body 34 in order to make the three elements join together by suitable, not illustrated, means of fixing.

The holding body 14 or handle has such a conformation as to be received inside the additional holding body 34 and to be able to slide longitudinally with respect to it when the device 10 is assembled.

Preferably the additional holding body 34 has a structure such as to identify two or more discrete positions of the holding body 14 or handle, for example corresponding to a closed, open and possibly intermediate position of the device 10. According to one possible embodiment for example illustrated in the FIGS. 1-4A, the additional holding body 34 comprises a setting ring 42 from which a curved wall 44 extends in a longitudinal direction with respect to the inner tube and the outer tube. According to one possible embodiment on the wall 44 are formed three circular ribs 46a, 46b, 46c which extend to form an incomplete circumference arch in such a manner as to receive and to allow the sliding of the handle 14. As a means of example by 46a has been indicated proximal ribbing, by 46b intermediate ribbing and by 46c distal ribbing, even if additional holding bodies with ribs differing in number, shape or arrangement can be envisaged.

With reference to the definition of the device according to the present invention, the inner tube and the outer tube define the elongated structure which develops between a proximal end and a distal end. The length of the elongated structure can vary. As a function of the materials with which the inner tube and the outer tube are made, the elongated structure can be semi-rigid or flexible. The arms 22 of the device 10 define means for locally dilating the walls of the anatomical structure of interest, associated with the distal end of the elongated structure. The control means comprise the inner tube and the outer tube which are slidable one with respect to and within the other and the means that cause this translation.

In the following is described the method of use of the embodiment of the above described diagnostic device.

The diagnostic device 10 is initially found in the closed position (FIG. 3), for example with the handle 14 located between the proximal ribbing 46a and the intermediate ribbing 46b, if present. The distal end of the outer tube 28 overlaps with the distal end of the inner tube 12. As a consequence, the arms 22 have enclosed or deformed distal ends forming a substantially "olive like" shape with the corresponding membrane 26.

The device 10 in the closed position is introduced transanally into the rectum/colon sigmoid/colon of the patient by the physician or the operator carrying out the examination. The degree of introduction of the device 10 can be verified using the radiopaque markers 33 on the outer tube 28, if present. The insertion of the device 10 is assisted by the "olive like" shape of the distal tip of the device itself, i.e. of the arms 22.

When the desired position is reached, the distal end of the device is opened "flower-like" in such a manner as to gradually enlarge the area of interest, as will be described in the following with reference to the embodiment in question.

The handle 14 is pushed towards the distal end of the device for example in such a manner to settle between the intermediate ribbing 46b and the distal ribbing 46c. In the meantime the additional holding body 34 is kept still with respect to the handle 14. As a consequence, the inner tube 12 translates by advancing with respect to the outer tube 28 and its distal end 12a begins to emerge with respect to the outer tube 28. A distal part of the arms 22 and of the corresponding membrane 26 emerges from the outer tube 28 and is free to enlarge elastically at least until in an intermediately open position of the device 10. In other words, the arms 22 initially maintained compressed by the outer tube 28 are free to expand, at least in correspondence with the part which is outside of the outer tube, consequently expanding the membrane 26. By this action the stretching and dilation of the walls of the colon and rectum are obtained.

The handle 14 may be rotated with respect to an axis longitudinal to the device 10 in order to block the device itself in an intermediate open position and allow the inspection of the area of interest. For example, by rotating the handle 14, the latter inserts itself at least partially between the intermediate ribbing 46b and the distal ribbing 46c in such a manner that the handle 14 and the inner tube 12 are not free to slide with respect to the additional holding body 34 and the outer tube 28.

In order to further open the device up to the totally open position, the handle 14 is repositioned in such a manner as to allow it to slide with respect to the additional holding body 34 and the outer tube 28. The handle 14 is pushed towards the distal end of the device 10, for example until reaching the position between the distal ribbing 46c and the setting ring 42 (FIG. 2), i.e. the totally open position. The distal end 12a of the inner tube 12 emerges further from the distal end 28a of the outer tube, freeing a greater distal part of the arms 22. The latter are therefore able to enlarge themselves further towards the exterior with the corresponding membrane, until reaching a substantially "cup-shaped" configuration. In the case wherein the distal end 12a of the inner tube emerges by a certain length from the distal end 28a of the outer tube 28, the free length of the inner tube defines a reaction surface for the arms 22 whilst the latter elongate themselves towards the exterior.

Even in this position, it is possible to block the handle 14 in order to allow the inspection of the area of interest, for example by rotating the handle as described above.

The above described operations in order to open the distal end of the device 10, wherein pushing the handle 14 is envisaged and therefore the inner tube 12 with respect to the additional holding body 34 and the outer tube 28, can be carried out analogously by pulling the additional holding body 34 and therefore the outer tube 28 toward the operator.

The above described device 10 may be used in association with viewing equipment (for example laparoscopes) introduced into the inner tube 12 and which, thanks to the opening of the arms 22, can be directed towards the appropriately enlarged area of interest in such a manner that the operator (physician) can check for the presence and the extent of the various pathologies. In other words the inner tube 12 allows the passage of illuminating and optical elements for the viewing of the area of interest.

Alternatively, the device 10 can be associated with an apparatus supplied with a colon-scope and insufflation device available from specialist medical practitioners.

By gradually and selectively enlarging the distal end of the device 10 it is for example possible to check the response by the mucosa whilst the patient mimes the process of defecation.

The present device allows the diagnosis of various pathologies amongst which intussusception, stenosis, prolapse, rectocele. The location and the dimensions of the defect can be quantified using the markers arranged on the device 10 and its arms 22.

The device 10 can additionally be moved backwards or forwards during the opening and closing of the same in order to allow the analyses of the various sections of tissues and in order to diagnose the conditions of the prolapse.

The closing of the distal tip of the device 10 occurs analogously to that described above, obviously with operations contrary to those performed in the opening of the same. During the withdrawal of the inner tube 12 with respect to the outer tube 28 (arrow F' of FIG. 3), the outer tube gradually encloses the arms 22 refolding them until reaching the closed configuration. The membrane 26 contracts following the arms 22.

From that above one can appreciate how envisaging a diagnostic device according to the present invention allows to have available a low cost device useful in the diagnosis of pathologies of tubular anatomical structures such as colorectal tracts. For example it is possible to identify and evaluate pathologies such as intestinal blockages, intussusception, stenosis, prolapse and rectocele.

The ability to carry out the diagnosis and quantification of a rectal prolapse is particularly advantageous given that the known devices, in particular colonoscopes, do not allow the diagnosis of such a pathology. Indeed colonoscopes require insufflation of air which provokes rectal dilation and consequently the disappearance of the mucosal prolapse.

Besides that above, the diagnostic device according to the present invention reduces patient discomfort and can be used even without the administration of sedatives, being much easier to introduce with respect to the known devices and does not require the insufflation of air.

An additional advantage of the diagnostic device according to the present invention is linked to the self-contained size in which it can be made, eliminating the drawbacks of the direct vision anoscopes which are painful and require the relaxation of the sphincter in that they have rather larger dimensions.

Further to that above, the diagnostic device according to the present invention can also be used on an outpatient basis, or in any case in non hospital or clinical environments, being a simple structure, easy to use and having a low cost, and which does not require the administration of sedatives.

In particular the providing of a tip or head or distal end which is non traumatic both during insertion in the closed position and during use in the open position is particularly advantageous.

Furthermore, the risk that the tissue will sag or that it can be caught in the jaws of the device is minimised or even eliminated.

The variety of materials with which both the inner tube and the outer tube can be made also allows the attainment of a relatively flexible elongated structure, adapted to being easily introduced in particular up to the sigmoidal colon.

The use of radiopaque markers, both on the outer tube and on the arms allow respectively to quantify the depth of insertion of the device and to quantify the prolapse.

The conformation of the device allows, in the closed position, the limiting of the risk that extraneous elements can introduce themselves into the interior of the device itself.

The shape reached in the totally open position is particularly advantageous for initiating a response from the sphincter. In addition, the shape of the arms 22 is preferably designed so as to have maximum radial opening at the distal end of the device.

It is clear that variations and/or additions to that described and illustrated above can be envisaged.

With reference to the previously described embodiment, alternatively to how it is represented in the figures, the additional holding body 34 can be constituted by a setting ring 42 alone without envisaging areas corresponding to defined degrees of openness of the device. Alternatively, ribs differing in number to that illustrated may be envisaged in order to define one or more predefined positions.

The arms 22 can be arranged completely inside the outer tube 28, when the device is found in the closed position, or protrude in a manner different to that illustrated. Furthermore, the inner tube 12 can be made in such a manner as to remain inside the outer tube 28 even in the completely open position of the device.

The fixing of the arms 22 or the membrane 26 to the inner tube 12 can be of various natures, for example without envisaging the grooving 24 or by envisaging it in a different shape to that illustrated.

The outer tube can be made in a single piece rather than in two parts as is illustrated.

The fixing between the inner tube 12 and the handle 14 (and possibly the fixing ferrule 16) or between the outer tube 28 and the additional holding body 34 (and possibly the fixing ferrule 36) can be of various natures even different to that illustrated.

The shape, both of the inner tube and of the outer tube can vary with respect to that described and illustrated.

The elastic or in any case expandable arms 22 due to the inherent characteristics of the materials with which they have been made can also be associated with other types of translation control for the inner tube 12 with respect to the outer tube 28. For example rotating controls or geared controls can be used analogous to those which will be described in the following with reference to additional embodiments of the diagnostic device according to the present invention.

Analogously, the control with a handle for the translation of the inner tube 12 with respect to the outer tube 28 may be used with different embodiments of the distal end, for example with rigid or elastic petals analogous to those which will be described in the following with reference to additional embodiments of the diagnostic device according to the present invention.

FIGS. 5-10 illustrate a possible additional embodiment of the diagnostic device according to the present invention. For simplicity of presentation, the diagnostic device shown in the FIGS. 5-10 has been generally indicated by the reference number 100.

By 102 an inner tube of preferably cylindrical shape and hollow inside has been indicated. The inner tube 102 is for example made from semi-rigid or flexible material, for example plastic material.

The inner tube 102 extends between a proximal end 102a and a distal end 102b. According to one possible embodiment, a part of the external surface of the inner tube 102 has a threaded length 104 close to the proximal end 102a. According to one possible embodiment a part of the external surface of the inner tube 102 has a circular groove 106 close to the distal end 102b.

The wall defining the inner tube 102 has in addition at least one aperture 108 elongated according to a longitudinal direction to the tube itself. In the example shown, two diametrically opposed rectangular apertures 108 are envisaged with their longer sides parallel to the longitudinal axis of the inner tube 102. Preferably the apertures 108 are formed in a proximal section of the inner tube 102 comprised between a threaded length 104 and the distal end 102b.

A proximal section of the inner tube 102 is operatively associated with a holding body 110, for example in the form of a knob.

Figure 6:
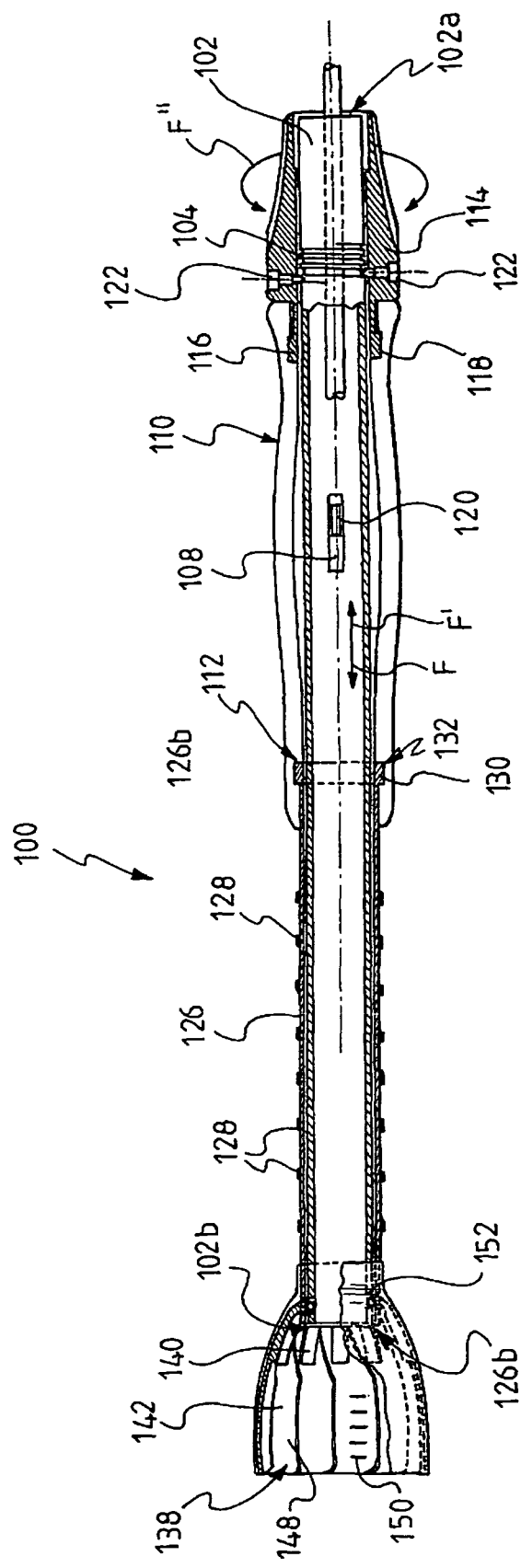
FIG. 6 shows a longitudinal sectional side view of the diagnostic device from FIG. 5.

The knob 110 comprises a first part 112 and a second part 114 associated with each other in such a manner that the second part 114 can rotate with respect to the first (arrow F" of FIGS. 6, 8, 9). According to one possible embodiment, the second part 114 comprises a flange 116 adapted to being housed within a circular seat 118 of the first part 112. According to one possible embodiment, the first part 112 is made in two semi-hulls adapted to being fixed, one with respect to the other, on the inner tube 102.

By 120 has been indicated a fin formed in the interior wall of the first part 112 and extending towards the inside of the holding body 110. The fin 120 is adapted to being inserted into the corresponding aperture 108 of the inner tube 102 remaining free to slide longitudinally for a length inside it. In the case that two apertures 108 are envisaged, analogously, two fins 120 are envisaged each adapted to being inserted into the respective aperture. In the case in which the first part 112 of the holding body 110 is made in two semi-hulls, advantageously each semi-hull comprises a fin 120.

The second part 114 comprises at least one pivot 122 which extends in a transverse direction with respect to the longitudinal development of the inner tube 102 and of the holding body 110, towards the interior of the second part itself. Preferably, two pivots 122 are envisaged arranged in diametrically opposite areas of the second part 114. According to one possible embodiment, the pivot 122 is inserted into a seat 124 on the second part 114 in such a manner as to protrude inside the second part itself. The end of the pivot 122 which extends inside the second part 114 is adapted to engage with the threaded length 104 of the inner tube 102.

By 126 has been indicated an outer tube adapted to positioning itself over the inner tube 102 at the level of a distal part of the inner tube itself. Also with reference to the outer tube 126 it is possible to identify a proximal end indicated by 126a and a distal end indicated by 126b. According to one possible embodiment, the outer tube 126 is for example made of semi-rigid or flexible material, for example plastic material.

Figure 7:
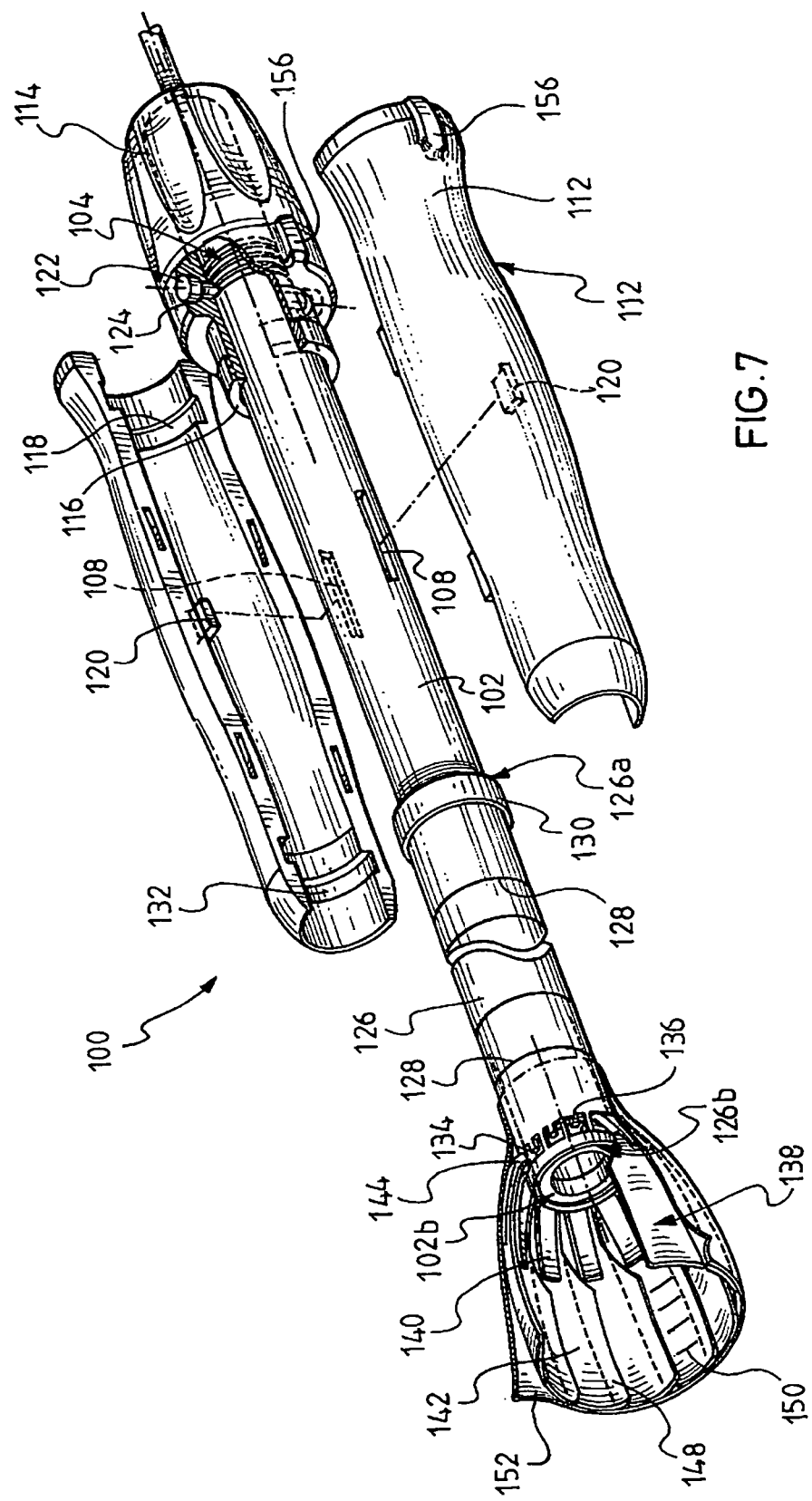
FIG. 7 shows a partially exploded perspective view of the diagnostic device from FIG. 5, where several details have been omitted in order to enhance other ones.
Figure 10:
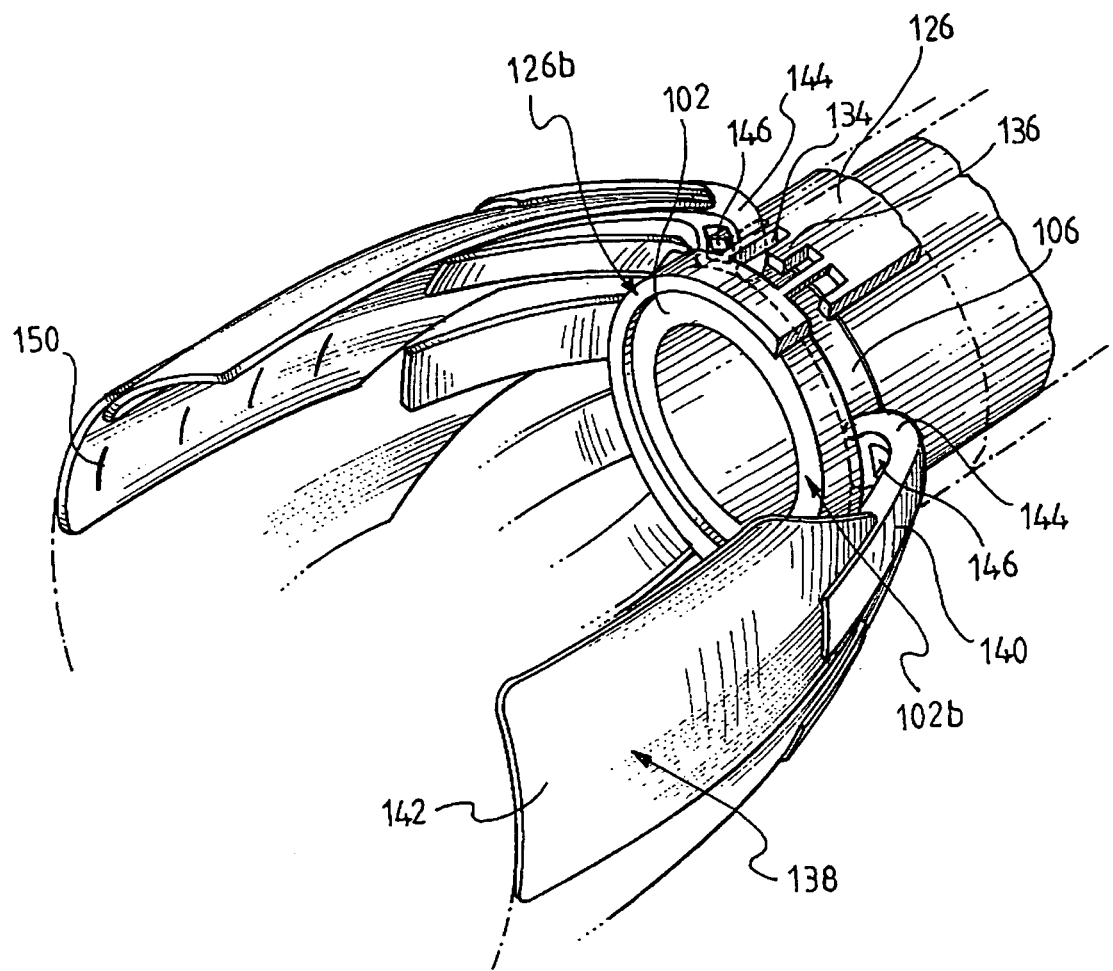
FIG. 10 shows an enlarged perspective view of a detail of the diagnostic device from FIG. 5.
Figure 11:
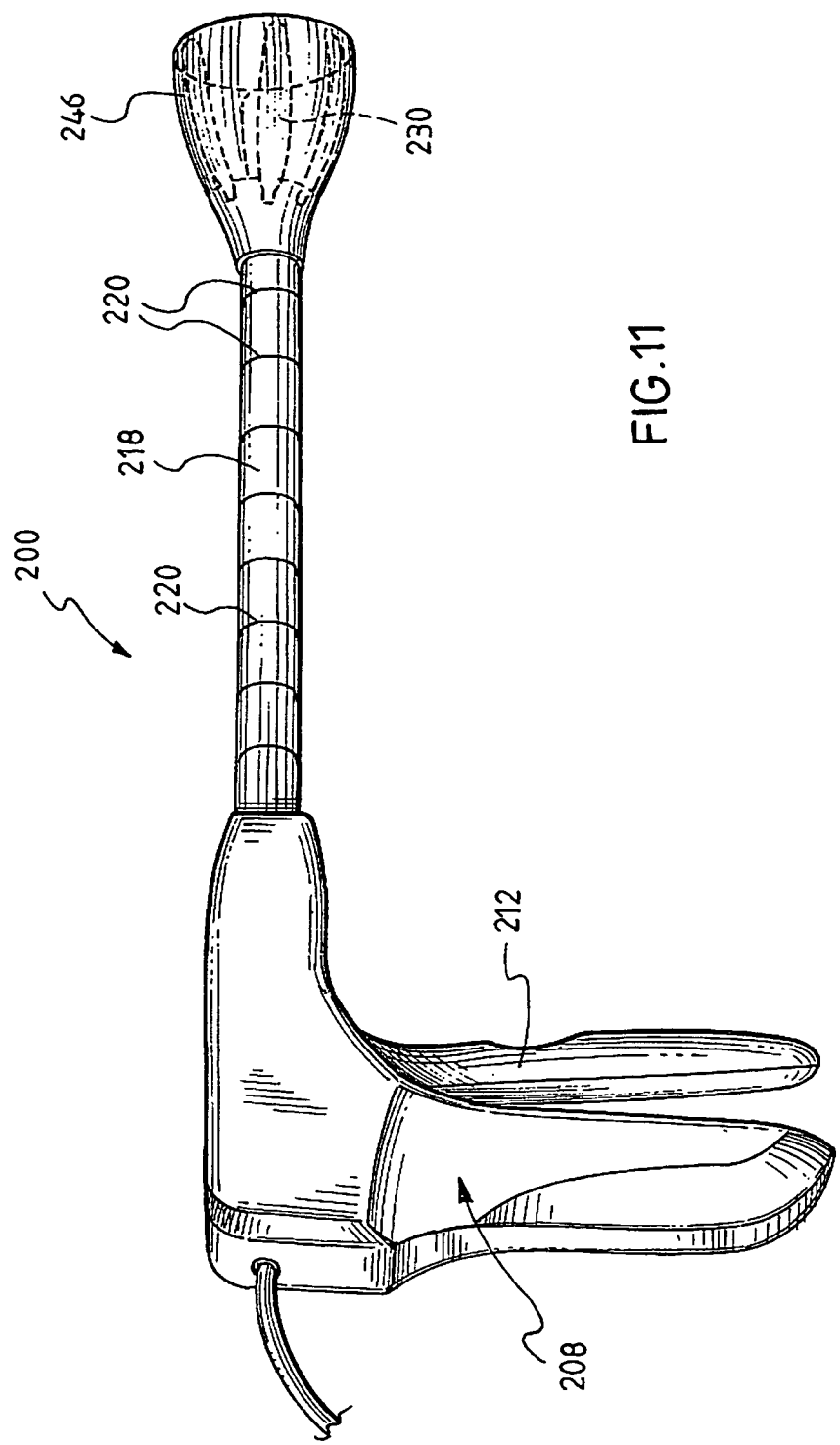
FIG. 11 shows a perspective view of an embodiment of the diagnostic device according to the present invention.
Figure 16:
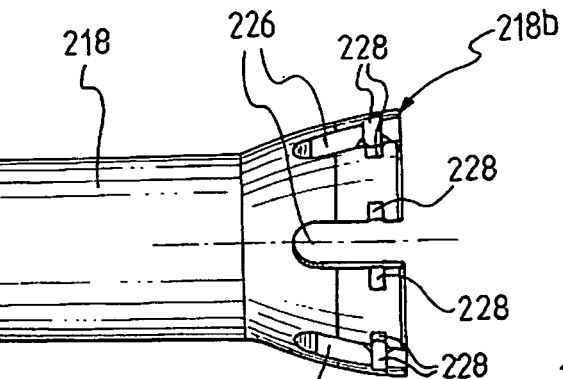
FIG. 16 is an enlarged side view of a detail of the diagnostic device from FIG. 11.

According to one possible embodiment, the outer tube 126 can have one or more detection elements or markers 128, for example distributed along the length of the outer tube itself in order to quantify the length of penetration of the instrument inside the anus. According to one possible embodiment, the markers 128 are in the shape of rings transversally arranged with respect to the outer tube and distributed along its length. In FIGS. 6 and 7 as an example some markers have been shown even if they could be provided in shape, number and arrangement different from what has been illustrated.

According to one possible embodiment, the proximal end 126a of the outer tube 126 has a flange 130 adapted to being housed within a circular seat 132 formed within the holding body 110, in particular within the first part 112.

According to one possible embodiment, the outer tube 126 has apertures 134 distributed along one circumference arranged in proximity to the distal end 126b of the outer tube itself. Each aperture 134 has one notch 136 which extends for example from a proximal edge of the aperture 134 towards a distal edge of the same.

The distal ends of the inner tube 102 and the outer tube 126 are operatively associated with petals 138 which preferably extend in a longitudinal direction with respect to the device 100.

According to one possible embodiment, the petals 138 are arranged in such a manner that their first end is associated with the distal end of the inner tube and the outer tube whilst a second end protrudes with respect to the aforementioned end.

The petals 138 are adapted to assuming at least two extreme configurations corresponding to a closed configuration and a completely open configuration.

According to one possible embodiment, a petal 138 comprises an arm 140 which broadens into a curved surface 142. The arm 140 has an end part 144 which refolds itself by almost 90° with respect to the development of the arm and wherein an aperture 146 is formed. According to one possible embodiment, the curved surface 142 has an asymmetric conformation with respect to the arm 140, with a side extension 148 in a transverse direction with respect to the longitudinal development of the device 100.

The end part 144 of the arm 140 is adapted to being housed within the circular groove 106 of the inner tube 102. Furthermore, the arm 140 is adapted to being inserted into one of the apertures 134 of the outer tube 126, with the notch 136 which inserts inside the aperture 146 of the arm 140.

According to one possible embodiment, the petals 138 have, preferably at their interior, detection elements or radiopaque markers 150. For example all the petals 138, or only some of them, can have one or more markers 150 distributed along the length of the petal itself in order to measure the nature of the pathology encountered. For example the markers 150 have been shown in one of the petals even if they may be provided on every petals or only in some of them. Moreover as an example the markers have been shown as lines transversal to the development of the petals and distributed along the length of the petal itself even if they may be provided in number, shape and arrangement different from what has been shown as an example.

According to one possible embodiment, a membrane 152 preferably made of an elastic or foldable material is placed over the distal end 126b of the outer tube 126 and externally to the petals 138. According to one possible embodiment, the membrane is made from transparent material.

In the assembled and closed configuration of the device 100, the petals 138 overlap each other, in particular the extension 148 of a petal positions itself externally to the curved surface 142 of the immediately adjacent petal.

According to one possible embodiment an introductory element 154 can be inserted into the inner tube 102 until protruding slightly from the distal part of the device. The distal end of the introductory element 154 has a conical conformation or is in any case adapted to limiting patient discomfort.

With reference to the definition of the device according to the present invention, the inner tube and the outer tube define the elongated structure which develops between a proximal end and a distal end. The length of the elongated structure can vary. As a function of the material with which the inner tube and the outer tube are made, the elongated structure can be semi-rigid or flexible. The petals 138 define the means for locally dilating the walls of the tubular anatomical structure associated with the distal end of the elongated structure. The control means comprise the inner tube and the outer tube which may slide one in respect to the other and one within the other and the means which cause this translation.

The method of use of the embodiment of the above described diagnostic device will be described in the following. In general terms, it is analogous to that of the previously described embodiment. In other words, the relative translation of the inner tube and of the outer tube gradually change the configuration of the distal end of the device from a closed configuration (FIG. 8) to a completely open configuration (FIG. 9) and vice versa.

In the above described embodiment, the relative translation between the inner tube and the outer tube is obtained by making the second part 114 of the holding body 110 rotate with respect to the first part 112 whilst the operator firmly holds the first part 112. During the rotation of the second part 114, the pivots 122 which are engaged within the threaded length 104 of the inner tube cause its translation with respect to the outer tube in advancement or withdrawal (arrows F and F' of FIGS. 6, 8, 9) as a function of the direction of rotation of the first part 114 (arrow F'' of FIGS. 6, 8, 9). The rotation of the inner tube 102 is impeded by the coupling between the fins 120 of the holding body 110 and the apertures 108 of the inner tube 102. The greater longitudinal extension of the aperture 108 with respect to that of the fins 120 instead allows the translation of the inner tube 102 with respect to the holding body 110 and the outer tube 126.

The relative translation between the outer tube 126 and the inner tube 102 causes the rotation of the petals 138 around a fulcrum constituted by the notches 136. In other words, making the inner tube advance in order to open the petals, the end part 144 of the petals 138 is drawn forward by the interaction with the circular groove 106 of the inner tube 102 with the consequence that the petal rotates around the respective notch 136 (arrow F''' of FIG. 9).

Analogously, the withdrawal of the inner tube 102 with respect to the outer tube 126 draws the end sections 144 of the petals 138 and causes its rotation around the respective notches 136 (arrow F'''' of FIG. 8).

Detection elements 156 may be envisaged on the first part 112 and on the second part 114 in order to define at least one configuration of the device 100.

The mode of application and the introduction and viewing methodology is analogous to that described for the first embodiment illustrated (FIGS. 1-4A). In the case in which use of the introductory element 154 is envisaged, the latter is extracted from the diagnostic device 100 following positioning in order to allow the passage of the means of viewing.

The advantages set forth above are also valid for the additional above described embodiment. Furthermore, the presence of rigid petals adapted to being made to rotate in order to stretch and widen the walls of the colon/rectum makes the operability of the device independent of the elasticity of the materials used for the arms 22.

It is clear that variations and/or additions to that described and shown above may be envisaged.

The apertures 108 of the inner tube 102 or the apertures 146 of the petals 138 may also not be passing through the entire thickness of the material as has been illustrated.

The coupling between the threaded length 104 and the second part 114 can be made by means other than the pivots 122 illustrated.

The petals 138 as described and their coupling to the distal end of the inner tube and the outer tube can also be envisaged with other control means for the relative translation between the inner tube and the outer tube. For example means analogous to the first embodiment illustrated (FIGS. 1-4) or means analogous to the embodiment which will be subsequently described may be envisaged.

Analogously, the means which control the relative translation between the inner tube and the outer tube such as described above can be associated with different means in order to enlarge the distal end of the device. For example arms analogous to those described in the first embodiment (FIGS. 1-4) or petals analogous to those which will be described in the following with reference to an additional embodiment of the diagnostic device may be envisaged.

With reference to FIGS. 11-17, a possible additional embodiment of the diagnostic device according to the present invention is illustrated. For simplicity of presentation, the diagnostic device illustrated in the FIGS. 11-17 has been generally indicated by the reference 200.

By 202 has been indicated an inner tube of preferably cylindrical shape and internally hollow. The inner tube 202 is for example made from semi-rigid or flexible material, for example in plastic material.

The inner tube 202 extends between a proximal end 202a and a distal end 202b. According to one possible embodiment, a part of the external surface of the inner tube 102 has a proximal grooved length 204 or a threaded length in proximity to the proximal end 202a. According to one possible embodiment a part of the external surface of the inner tube 202 has a distal grooved length 206 or a threaded length in proximity to the distal end 202b.

A proximal part of the inner tube 202 is operatively associated with a holding body 208, for example in the shape of a pistol.

The pistol 208 comprises a support structure 210, for example formed from two semi-hulls, which house a trigger 212. This latter is riveted into the support structure 210 and kept in the resting position, corresponding to the closed position of the device 200, by spring means 214, for example a helical spring. The trigger 212 comprises a toothed area 216 adapted to coupling with the grooved length 204 of the inner tube 202.

By 218 has been indicated an outer tube adapted to positioning itself over the inner tube 202 at the level of a distal part of the inner tube itself. Also with reference to the outer tube 218 it is possible to identify one proximal end indicated by 218a and one distal end indicated by 218b. According to one possible embodiment, the outer tube 218 is made from semi-rigid or flexible material, for example in plastic material.

According to one possible embodiment, the outer tube 218 may have one or more detection elements or markers 220, for example distributed along the length of the outer tube itself in order to quantify the length of penetration of the device inside the anus. In the figures as an example have been shown markers having the shape of rings transversal to the longitudinal development of the tube and distributed along its length even if they could be provided in number, shape and arrangement different from what has been illustrated.

According to one possible embodiment, the proximal end 218a of the outer tube 218 has a flange 222 adapted to being housed within a circular seat 224 formed within the holding body 208, in particular within the supporting structure 210.

According to one possible embodiment, the outer tube 218 has apertures 226 (FIG. 16), for example longitudinal, distributed along the perimeter of the distal end 218b. According to one possible embodiment, the distal part of the outer tube 218 involved with the apertures 226 is of truncated conical shape, with the larger diameter located at the distal end 218b of the outer tube 218. according to one possible embodiment, seats 228 (FIG. 16) formed at the level of the edges opposite the apertures 226 are envisaged.

The distal ends of the inner tube 202 and the outer tube 218 are operatively associated with the petals 230 which extend preferably in a longitudinal direction with respect to the device 200.

According to one possible embodiment, the petals 230 are arranged in such a manner that their first end is associated with the distal ends of the inner tube and the outer tube whilst a second end protrudes with respect to the aforementioned ends.

The petals 230 are adapted to assuming at least two extreme configurations corresponding to a closed configuration (FIG. 13) and to an open configuration (FIG. 14).

According to one possible embodiment, a petal 230 comprises an arm 232 which broadens into a curved surface 234. According to one possible embodiment, the curved surfaces of the petals extend transversally in such a manner as to not overlap each other reciprocally when the device finds itself in the open position.

Figure 15:
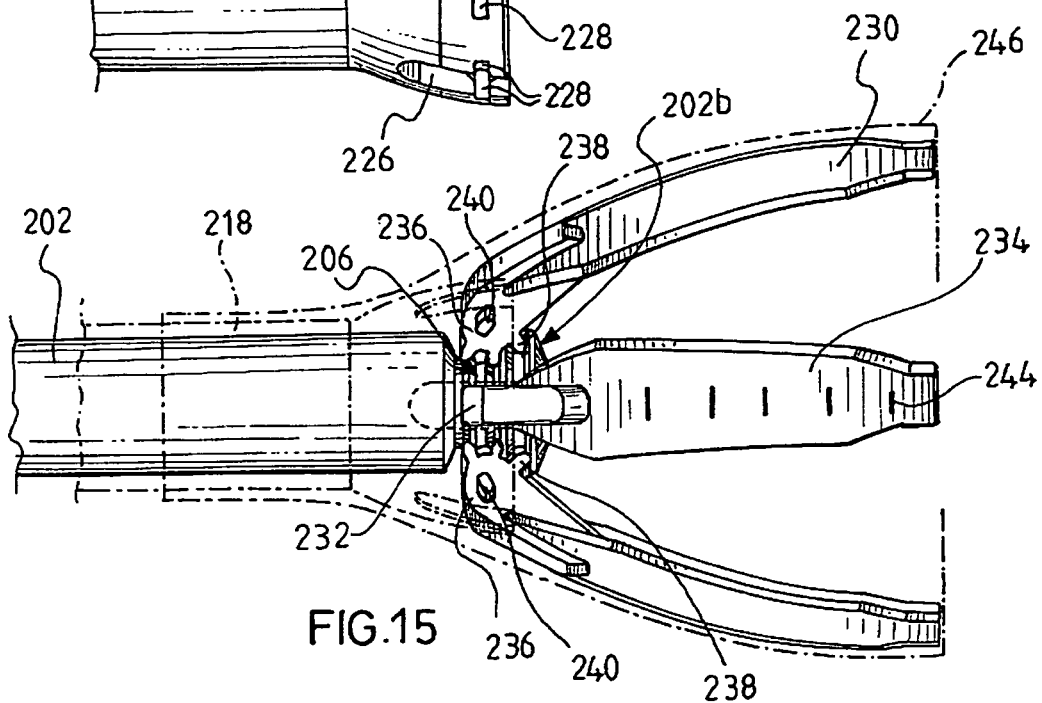
FIG. 15 is an enlarged side view of a detail of the diagnostic device from FIG. 11 where several details have been represented with a dash-dot line.
Figure 17:
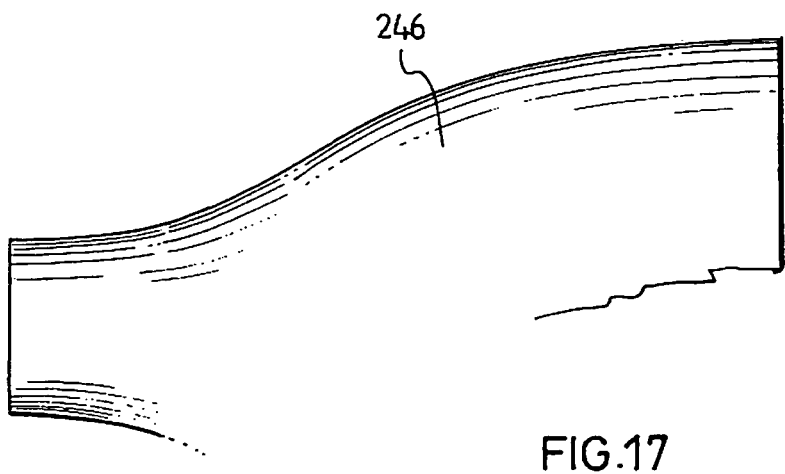
FIG. 17 is a partial enlarged side view of a detail of the diagnostic device from FIG. 11.
Figure 18:
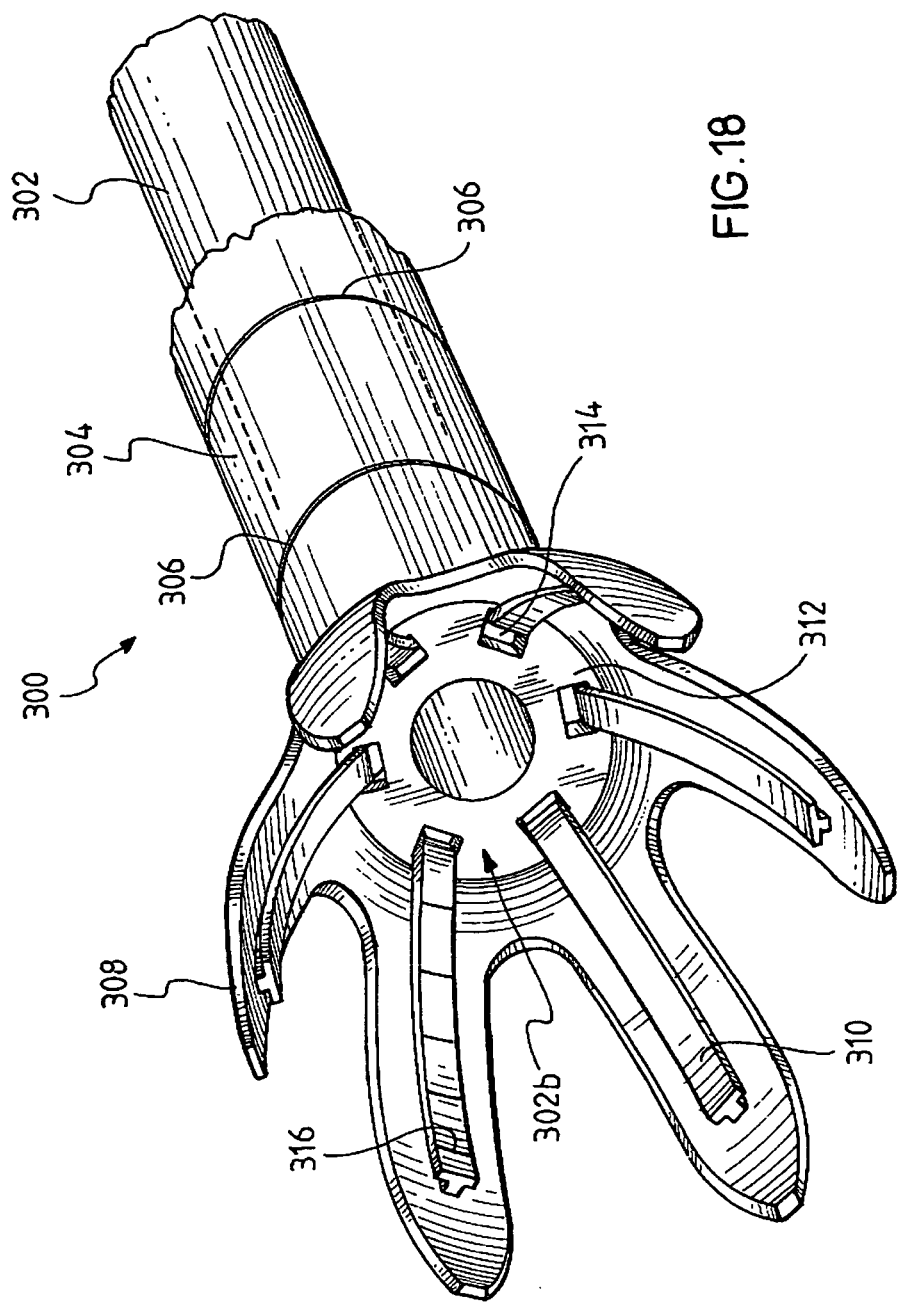
FIG. 18 is a perspective view of a detail of a possible embodiment of the diagnostic device according to the present invention.
Figure 19:
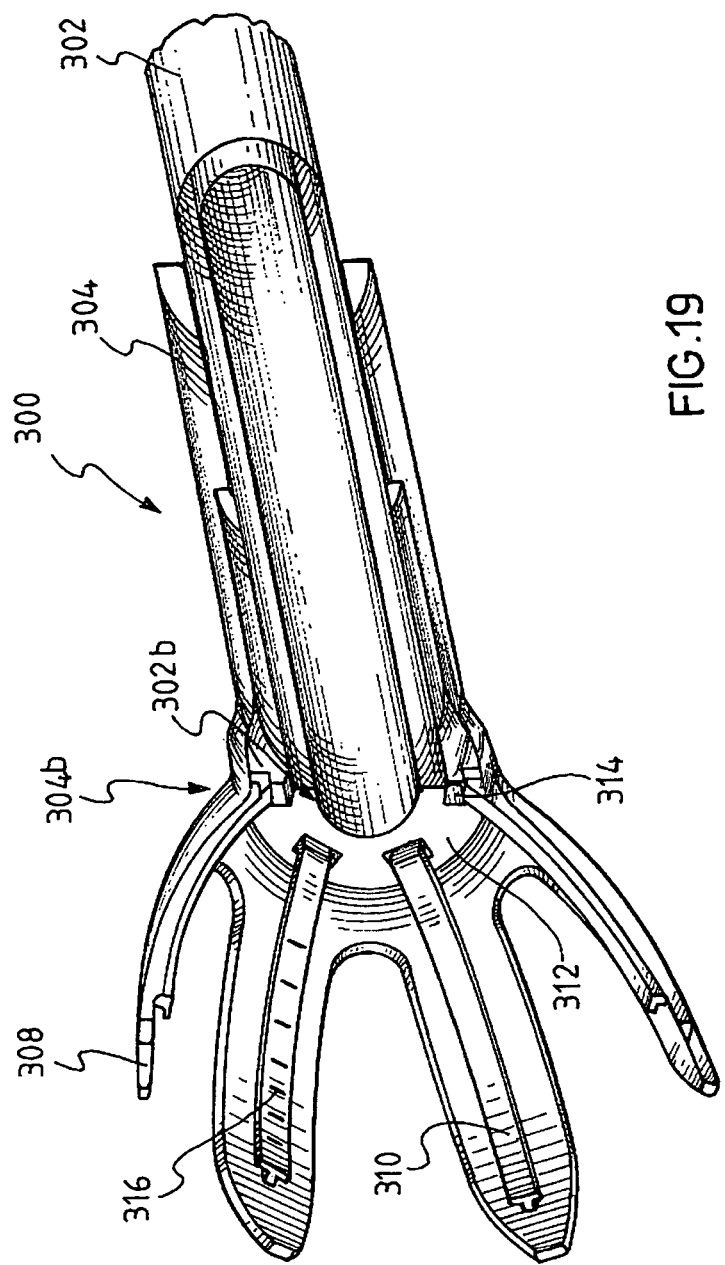
FIG. 19 is a partially sectional perspective view of the detail from FIG. 18.

The arm 232 has an end position 236 which comprises a toothed area 238 (FIG. 15). According to one possible embodiment, at the level of the end part 236 of the petal 230 a pivot 240 is envisaged which extends transversally towards the arm 232 from both sides of the petal itself.

The end part 236 of the arm 232 is adapted to being housed within an aperture 226 of the outer tube 218, preferably in such a manner that the pivot 240 is housed within the respective seats 228. In addition the toothed area 238 is adapted to coupling with the distal grooved length 204 of the inner tube 202.

According to one possible embodiment, the petals 230 have identifying elements or radiopaque markers 244 preferably in their interior. For example all the petals 230, or only some of them, can have one or more markers 244 distributed along the length of the petal itself in order to measure the nature of the pathology encountered. For example the markers 244 have been shown in only one of the petals and they have been shown as lines transversal to the development of the petals and distributed along the length of the petal itself. Obviously markers arranged on all the petals or only on some of them or markers made in shape, number or arrangement different from what has been shown could be provided.

According to one possible embodiment, a membrane 246 preferably made from elastic or refoldable material is placed over the distal end 218b of the outer tube 218 and externally to the petals 230, thus finishing the "cup" shape of the distal and in the open configuration. According to one possible embodiment, the membrane is made of transparent material.

According to one possible embodiment an introductory element, not shown, can be inserted into the inner tube 202 until protruding slightly from the distal part of the device. The distal end of the introductory element has a conical conformation or is however adapted to limiting patient discomfort.

With reference to the definition of the device according to the present invention, the inner tube and 15 the outer tube define the elongated structure which develops between a proximal end and a distal end. The length of the elongated structure can vary. As a function of the materials with which the inner tube and the outer tube are made, the elongated structure can be semi-rigid 20 or flexible. The petals 230 define the means for locally dilating the walls of the tubular anatomical structure associated with the distal end of the elongated structure. The control means comprises the inner tube and the outer tube which can slide one with respect to the other and one within the other and the means which cause this translation.

The mode of use of the embodiment of the above described diagnostic device is described in the following. In general terms it is analogous to that of the previously described embodiment. In other words, the relative translation of the inner tube and the outer tube gradually alter the configuration of the distal end of the device from a closed configuration (FIG. 13) to a completely open configuration (FIG. 14), and vice versa.

In the above described embodiment, the relative translation between the inner tube and the outer tube is obtained by making the trigger 212 which couples with the grooved length 204 of the inner tube 202 rotate. As a function of the direction of rotation of the trigger the advancement or withdrawal (arrow F or F') of the inner tube with respect to the outer tube and respectively the opening or closure of the petals 230 is obtained.

The relative translation between the outer tube and the inner tube causes the rotation of the petals 230 around the pivot 240, caused by the coupling between the distal grooved length 206 and the toothed area 238 of the petals 230. In other words, by making the inner tube advance in order to open the petals, the end section 236 of the petals 230, and in particular the toothed area 238 is made to rotate by the interaction with the additional grooved length 206 of the inner tube 202 with the consequence that the petal rotates around the respective pivot 240 (F'").

Analogously, by releasing the trigger 212, the latter is recalled by the spring means 214 causing the withdrawal of the inner tube 202 with respect to the outer tube 218. Such relative translation causes the rotation of the toothed area 238 of the petals 230 causing its rotation around the respective pivot 240 (F"").

The mode of application and the introduction and viewing methodology is analogous to that described for the first and second embodiment previously illustrated and described. In the case in which the use of the introductory element is envisaged, this latter is extracted from the diagnostic device 200 following positioning in order to allow the passage of the means of viewing.

The advantages set forth above also find validity in the additional above described embodiment. In addition, the presence of rigid petals adapted to being made to rotate in order to stretch and widen the walls of the colon/rectum make the operation of the device independent of the elasticity of the materials used for the arms 22.

It is evident that variants and/or additions to that described and illustrated above can be envisaged.

The petals 230 can be for example analogous to the petals 138 of the second embodiment (FIGS. 5-11). In particular, a curved surface 234 extends from the arm 232 having an asymmetrical conformation with respect to the arm itself, with a side extension 242 in a transverse direction with respect to the longitudinal development of the device 200. In the assembled and closed configuration of the device 200, the petals 230 overlap one another, in particular the extension 242 of each petal is arranged externally to the curved surface 234 of the petal immediately adjacent. As a consequence, in the assembled and open configuration of the device, the petals themselves define the "cup-shaped" conformation of the distal end.

The petals 230 as described thus and in their coupling with the distal end of the inner tube and the outer tube can also be envisaged with other control means for the relative translation between the inner tube and the outer tube. For example, means analogous to the first or to the second embodiment illustrated may be envisaged.

Analogously, the means which control the relative translation between the inner tube and the outer tube as thus described above can be associated with different means for enlarging the distal end of the device. For example, arms analogous to those described in the first embodiment (FIGS. 1-4A) or petals analogous to those described in the second embodiment may be envisaged.

With reference to the FIGS. 18-21, there is illustrated a possible further embodiment of the distal end of the diagnostic device according to the present invention. For simplicity of presentation, the diagnostic device shown in FIGS. 18-21 has been overall indicated with the numeral 300.

By 302 has been designated an inner tube preferably of a cylindrical shape and hollow therein. The inner tube 302 may be for example in a semi-rigid or flexible material, for example in plastic material.

The inner tube 302 extends between a proximal end, not shown, and a distal end 302b.

By 304 has been designated an outer tube 20 suitable to be arranged on the inner tube 302 at at least one distal portion of the inner tube. Also with reference to the outer tube 304 it is possible to identify a proximal end, not shown, and a distal end designated by 304b. According to a possible embodiment, the outer tube 304 is made in a semi-rigid or flexible material, for example in plastic material.

According to a possible embodiment, the outer tube 304 is made in a semi-rigid or flexible material, for example in plastic material.

According to a possible embodiment, the outer tube 304 may have one or more detection elements or markers 306, for example distributed along the length of the outer tube itself, in order to measure the length of penetration of the device inside the anus. According to a possible embodiment, the markers 306 have the shape of circular rings arranged transversal to the outer tube and distributed along the length thereof. The markers 306 may however be provided in shape, number and arrangement different from what has been illustrated.

The distal ends of the inner tube 302 and the outer tube 304 are operatively associated to petals 308, which extend preferably in a longitudinal direction relative to the device 300.

According to a possible embodiment, the petals 308 are arranged such that a first end thereof is associated with the distal ends of the inner tube and the outer tube while a second end protrudes relative to said ends. Particularly, the petals 308 are made as one piece with the outer tube 304. In other words, the outer tube 304 extends to form the petals 308.

The petals 308 are adapted to assuming at least two estreme configurations corresponding to a closed configuration and a completely open configuration.

According to a possible embodiment, each petal 308 couples with a portion of the inner tube 302 forming a unidirectional guide adapted to close or open the petals subsequent to the translation of the inner tube relative to the outer tube and the petals.

According to a possible embodiment, each petal comprises a longitudinally extended rib 310 and the inner tube 302 comprises a distal flange 312 provided with openings 314 adapted to couple with respective ribs 310 of the petals. In other words, the petals 308 and the inner tube 302 mutually couple by means of a shape coupling defining a restraint adapted to leave only one degree of freedom corresponding to the relative translation between the inner tube and the petals.

According to a possible embodiment, the rib 310 has a T-shaped cross section and the openings 314 have a C-shaped cross section suitable to couple with the cross-section of a respective rib 310.

In accordance with a possible embodiment, the petals 308 have, preferably at their interior, detection elements or radiopaque markers 316. For example, all the petals 308, or only some of them, can have one or more markers 316 distributed along the length of the petal itself in order to measure the nature of the pathology encountered. By way of example, in FIG. 18 there have been represented several markers 316 only on one of petals 308. The markers 316 may be however provided either on all petals or only on some of them. Furthermore, the markers 316 have been represented as lines transversal to the development of the petal and distributed along the length of the petal, though they may be provided in number and shape different from what has been shown.

In accordance with a possible embodiment, not shown, a membrane preferably made of an elastic or foldable material is placed over the distal end of the outer tube 304 and externally to the petals 308, thus finishing the "cup" shape of the distal end in the open configuration. According to a possible embodiment, the membrane is made in transparent material.

With reference to the definition of the device according to the present invention, the inner tube and the outer tube define the elongated structure developing between a proximal end and a distal end. The length of the elongated structure may vary. As a function of the material with which the inner tube and the outer tube are made, the elongated structure can be either semi-rigid or flexible. The petals 308 define the means for locally dilating the walls of the tubular anatomical structure associated with the distal end of the elongated structure. The control means comprise the inner tube and the outer tube which can slide one inside the other and the means which cause this relative translation.

The method for employing the embodiment of the above diagnostic device is described below. Generally, this is similar to the embodiments described above. In other words, the relative translation of the inner tube and the outer tube gradually change the configuration of the distal end of the device from a closed configuration to a completely open configuration and vice versa.

In the embodiment described above, the relative translation between the inner tube and the outer tube can be obtained by any means, for example using the means described in the other embodiments described.

The relative translation between the outer tube and the inner tube causes the distal flange 312 to slide relative to the petals, along the ribs 310. The petals are made of a resilient material such as to follows the movement of the inner tube. Particularly, the restraint between the inner tube and the petals causes the petals to approach each other and close while the inner tube is moving forward relative to the outer tube or the petals and, similarly, the petals to move apart and open while the tube is moving backward relative to the outer tube or the petals.

The application mode and method for introduction and visualization is similar to that described above for the previous embodiments. The advantages set forth above are also found in the further embodiment described above.

It should be understood that variations and/or additions to what has been described and illustrated above may be provided.

The shape of the petals may be different, for example similar to the petals 138 of the second embodiment (FIGS. 5-11). Furthermore, the coupling between the petals and the inner tube may come in a different shape, for example swallow-tailed or with other shape couplings allowing the inner tube and the petals to translate relative to each other.

Furthermore, the petals may not be formed as one piece with the outer tube and mounted on the distal end of the outer tube such as to open and close while the inner tube is moving forward or backward.

The petals 308 such as described and their coupling with the distal end of the inner tube and the outer tube can be also provided with other command or control means for the relative translation between the inner tube and the outer tube. For example, means similar to the other embodiments shown may be provided.

With reference to all the embodiments shown and described, there may be provided different means adapted to change the configuration of the means for locally dilating the walls of the tubular structure. For example, different means from an inner tube and an outer tube that can be relatively translated in order to change the configuration of the means for locally dilating the walls of the tubular structure.

To the preferred embodiments of the diagnostic device such as described above, those skilled in the art, aiming at satisfying contingent and specific requirements, may carry out a number of modifications, adaptations and replacement of elements with others functionally equivalent, without however departing from the scope of the claims below.

The invention claimed is:

1. A diagnostic device for pathologies of naturally occurring tubular anatomical structures comprising:
   a tubular elongated structure developing between a proximal end and a distal end and being adapted to be inserted in the tubular anatomical structure,
   wherein said elongated structure comprises an inner tube and an outer tube adapted to internally receive said inner tube,
   means for locally dilating the walls of the tubular anatomical structure being associated with the distal end of said elongated structure, said means for locally dilating being movable between a closed position for the introduction of the device and at least one open position for the viewing and evaluation of the pathology,
   wherein said means for locally dilating comprise petals being arranged such that one first end thereof is associated to the distal end of the elongated tubular structure, said petals being adapted to assume at least one closed configuration and one open configuration,
   said inner tube and said outer tube being suitable to translate relatively to each other to open or close said petals,
   control means being associated to the proximal end of the elongated structure, said control means being operatively connected to said means for locally dilating in order to move them between the closed position and the open position, and vice versa,
   wherein the outer tube comprises a thickened portion adjacent a proximal end thereof, and wherein in the region of the petals, the outer tube comprises a thinned portion that extends distally to form said petals and a flexure hinge at said first end of the petals in which the outer tube and the petals form together one continuous external surface, and each of said petals is coupled with a portion of said inner tube forming a unidirectional guide adapted to close or open the petals in response to the translation of the inner tube relative to the outer tube and the petals, and wherein each petal comprises a longitudinally extending rib, and wherein said inner tube comprises a distal flange provided with openings through which respective ribs of said petals are displaced.

2. The diagnostic device according to claim 1, further comprising means of viewing adapted to be associated with the elongated tubular structure and reach the tract of the tubular anatomical structure dilated by the means of dilating.

3. The diagnostic device according to claim 2, wherein the elongated tubular structure is internally hollow in order to receive the means of viewing.

4. The diagnostic device according to the claim 1, wherein one of the petals comprises at least one detection element or marker.

5. The diagnostic device according to claim 1, further comprising a membrane being externally arranged on the petals.

6. The diagnostic device according to claim 5, wherein said membrane is made in an elastic material.

7. The diagnostic device according to claim 5, wherein said membrane is made in a transparent material.

8. The diagnostic device according to claim 1, wherein an outer surface of the outer tube comprises at least one detection element or marker.

9. The diagnostic device according to claim 1, wherein said rib has a T-shaped cross-section and wherein said openings have a C-shaped cross-section suitable to couple with the cross-section of a respective rib.

10. The diagnostic device according to one of claim 1, wherein said inner tube comprises a holding body arranged at a proximal end of the inner tube and wherein said outer tube comprises a further holding body being arranged at a proximal end of the outer tube.

11. The diagnostic device according to claim 1, wherein said elongated structure is configured such that forward movement of said inner tube relative to said outer tube serves to close said petals.

12. A diagnostic device for pathologies of naturally occurring tubular anatomical structures comprising:

a tubular elongated structure developing between a proximal end and a distal end and being adapted to be inserted in the tubular anatomical structure, the tubular elongated structure including an inner tube and an outer tube, wherein the inner tube is received within the outer tube;

a plurality of petals formed circumferentially at a distal end of the outer tube such that the outer tube and the petals form together one continuous external surface, the petals being displaceable between a closed position for the introduction of the device and an open position for the viewing and evaluation of the pathology, wherein the inner tube and the outer tube are suitable to translate relatively to each other to open or close the petals; and a control mechanism associated to the proximal end of the elongated structure, the control mechanism being cooperable with the inner tube and the outer tube to displace the inner tube relative to the outer tube, wherein the outer tube is configured to define a flexure hinge for the petals, and wherein each of the petals comprises a longitudinally extending rib connected to and extending over a majority of a length of the petals and adapted to close or open the petals in response to translation of the inner tube relative to the outer tube and the petals.

13. The diagnostic device according to claim 12, wherein the outer tube comprises a thickened portion adjacent a proximal end thereof, and wherein the outer tube comprises a thinned portion that extends distally to form the petals and the flexure hinge.

* * * * *